US010532036B2

(12) United States Patent
Atkinson

(10) Patent No.: US 10,532,036 B2
(45) Date of Patent: Jan. 14, 2020

(54) COMBINATION COMPOSITION

(71) Applicant: AFT Pharmaceuticals Ltd, Auckland (NZ)

(72) Inventor: Hartley Campbell Atkinson, Auckland (NZ)

(73) Assignee: AFT Pharmaceuticals Limited, Auckland (NZ)

( * ) Notice: Subject to any disclaimer, the term of this patent is extended or adjusted under 35 U.S.C. 154(b) by 77 days.

(21) Appl. No.: 13/857,802

(22) Filed: Apr. 5, 2013

(65) Prior Publication Data

US 2014/0073696 A1    Mar. 13, 2014

Related U.S. Application Data

(63) Continuation of application No. 11/570,887, filed as application No. PCT/NZ2005/000168 on Jul. 7, 2005, now abandoned.

(30) Foreign Application Priority Data

Jul. 7, 2004   (NZ) ......................................... 533982

(51) Int. Cl.
  *A61K 31/192*  (2006.01)
  *A61K 31/167*  (2006.01)
(52) U.S. Cl.
  CPC .......... *A61K 31/192* (2013.01); *A61K 31/167* (2013.01)
(58) Field of Classification Search
  CPC .. A61K 2300/00; A61K 31/192; A61K 31/16; A61K 31/167; A61K 31/215; A61K 9/2059
  See application file for complete search history.

(56) References Cited

U.S. PATENT DOCUMENTS

| 5,260,337 | A  | 11/1993 | Sims et al.    |
| 5,409,709 | A  | 4/1995  | Ozawa et al.   |
| 5,854,226 | A  | 12/1998 | Penkler et al. |
| 6,440,983 | B1 | 8/2002  | Frank-Kollman  |
| 2008/0200549 | A1 | 8/2008 | Atkinson |
| 2008/0275125 | A1 | 11/2008 | Atkinson |
| 2009/0264530 | A1 | 10/2009 | Nickell |
| 2011/0166234 | A1 | 7/2011 | Atkinson |
| 2011/0275718 | A1 | 11/2011 | Atkinson |

FOREIGN PATENT DOCUMENTS

| AU | 605538 B | 7/1989 |
| CA | 1336687 C | 8/1995 |
| JP | 5-148139 A | 6/1993 |
| JP | 11-158066 A | 6/1999 |
| KR | 10-1997-000231 A | 1/1997 |
| WO | WO 2007/034135 A1 | 3/2001 |
| WO | WO 2006/004449 A2 | 1/2006 |

OTHER PUBLICATIONS

Rainsford et al 'Ibuprofen and Paracetamol: Relative Safety in Non-perscription Dosages' J. Pharm. Pharmacol., vol. 49, p. 345-376, 1997.*
American Society of Health-System Pharmacists, Inc., AHFS Drug Information 2004, Chapter 28, Central Nervous System Agents, Ibuprofen, pp. 1974-1980, Acetaminophen, pp. 2083-2091.
Bijlsma, J., "Analgesia and the Patient with Osteoarthritis," *American Journal of Therapeutics* 9(3):189-197, 2002.
Brustin, http://medi.ru/doc/1001.htm, 2001 (+ partial English translation) (13 pages total).
Carrive et al., Changes in formalin-evoked spinal Fos expression and nociceptive behaviour after oral administration of Bufferin A (aspririn) and L-5409709 (ibuprofen + caffeine + paracetamol), *Pain* 70:253-266, 1997.
Decision Granting Petition Under 37 CFR 1.138(d) and Notice of Abandonment for U.S. Appl. No. 12/896,052, dated Dec. 28, 2010 (3 pages).
Dutta G., et al., "Bioavailability of paracetamol and ibuprofen in single and combination dosage in rabbits," *Indian J Pharmacol* 36:43-4, 2004.
IR Edwards, Pharmacological Basis of Adverse Drug Reactions, Chapter 6, p. 293 in Avery's Drug Treatment, 1996, 4th Edition, Adis International, Auckland.
"Guidance for Industry, Estimating the Maximum Safe Starting Dose in Initial Clinical Trials for Therapeutics in Adult Healthy Volunteers," U.S. Dept. Health and Human Services, FDA, Center for Drug Evaluation and Research, Jul. 2005 (30 pages).
Homer et al., "Audit of pain management at home following tonsillectomy in children," *The Journal of Laryngology & Otology*, vol. 115, pp. 205-208, Mar. 2001.
International Preliminary Report on Patentability for PCT International Application No. PCT/NZ2005/000168, dated Jan. 9, 2007 (4 pages).
International Search Report for PCT International Application No. PCT/NZ2005/000168, dated Jan. 4, 2006 (4 pages).
Korean Drug Index, The Yakup Shinmoon, 2001 (3 pages).
Lal et al., Antipyretic Effects of Nimesulide, Paracetamol and Ibuprofen-Paracetamol, *Indian Journal of Pediatrics* 67(12):865-870, 2000.
Menhinick et al., "The efficacy of pain control following nonsurgical root canal treatment using ibuprofen or a combination of ibuprofen and acetaminophen in a randomized, double-blind, placebo-controlled study," *International Endodontic Journal* 37:531-541, 2004.
Middleton, "Double Blind Trial in General Practice Comparing the Efficacy of "Benylin Day and Night" and Paracetamol in the Treatment of the Common Cold," *The British Journal of Clinical Practice* 35(9):297-300, Sep. 1981.
Notice of Abandonment for U.S. Appl. No. 11/570,887, dated Apr. 17, 2013 (3 pages).
Notice of Abandonment and Interview Summary for U.S. Appl. No. 12/113,171, dated Oct. 8, 2010 (5 pages).

(Continued)

*Primary Examiner* — Jean P Cornet
(74) *Attorney, Agent, or Firm* — Fish & Richardson P.C.

(57) ABSTRACT

A combination pharmaceutical composition for the treatment of pain including about 125 mg to about 150 mg ibuprofen and about 475 mg to about 500 mg paracetamol.

4 Claims, No Drawings

(56) References Cited

OTHER PUBLICATIONS

Notice of Abandonment for U.S. Appl. No. 12/113,171, dated May 9, 2011 (3 pages).
Notice of Abandonment for U.S. Appl. No. 12/924,812, dated Jun. 4, 2012 (2 pages).
Office Action for U.S. Appl. No. 11/570,887, dated Oct. 9, 2009 (8 pages).
Office Action for U.S. Appl. No. 11/570,887, dated Jun. 7, 2010 (10 pages).
Office Action for U.S. Appl. No. 12/113,171, dated Mar. 30, 2010 (10 pages).
Office Action for U.S. Appl. No. 12/924,812, dated Nov. 25, 2011 (9 pages).
Official Communication (Examiners Answer to Appeal Brief filed Nov. 8, 2010) for U.S. Appl. No. 11/570,887, dated Feb. 3, 2011 (11 pages).
Official Communication (Reply Brief Noted) for U.S. Appl. No. 11/570,887, dated Apr. 18, 2011 (2 pages).
Official Communication for U.S. Appl. No. 11/570,887, dated Apr. 22, 2011 (2 pages).
Official Communication for U.S. Appl. No. 11/570,887, dated Feb. 6, 2013 (11 pages).
Pickering et al., "Double-blind, placebo-controlled analgesic study of ibuprofen or rofecoxib in combination with paracetamol for tonsillectomy in children," *British Journal of Anaesthesia* 88(1):72-77, Jan. 2002.
Rainsford et al., "Ibuprofen and Paracetamol: Relative Safety in Non-prescription Dosages," *J. Pharm. Pharmacol.* 49:345-376, 197.
Restriction Requirement for U.S. Appl. No. 11/570,887, dated Jul. 13, 2009 (7 pages).
Restriction Requirement for U.S. Appl. No. 12/113,171, dated Nov. 2, 2009 (7 pages).
Restriction Requirement for U.S. Appl. No. 12/924,812, dated Oct. 19, 2011 (6 pages).
Scheiman et al, "A Randomized, Controlled Comparison of Ibuprofen at the Maximal Over-the-Counter Dose Compared With Prescription-Dose Celecoxib on Upper Gastrointestinal Mucolsal Injury," Clin. Gastroenterol. Hepatol. 2(4):290-5, 2004.
Seymour et al., "An investigation into the comparative efficacy of soluble aspirin and solid paracetamol in postoperative pain after third molar surgery," *British Dental Journal* 194(3):153-157, Feb. 8, 2003.
Swallow, Janet, "Pain at home: children's experience of tonsillectomy," *Journal of Child Health Care* 4(3):93-98, Autumn 2000.
Viitanen et al., "Analgesic efficacy of rectal acetaminophen and ibuprofen alone or in combination for paediatric day-case adenoidectomy," *British Journal of Anaesthesia* 91(3):363-367, Sep. 2003.
Written Opinion for PCT/NZ2005/000168, dated Jan. 4, 2006 (3 pages).
Craen, et al., "Analgesic efficacy and safety of paracetamol-codeine combinations versus paracetamol alone: a systematic review," BMJ, 313:321-325, 1996.
Dahl, et al., "Ibuprofen vs. acetaminophen vs. ibuprofen and acetaminophen after arthroscopically assisted anterior cruciate ligament reconstruction," European Journal of Anaesthesiology, 21(6):471-475, 2004.
Doherty, et al., "A randomised controlled trial of ibuprofen, paracetamol or a combination tablet of ibuprofen/paracetamol in community-derived people with knee pain," Annals of the Rheumatic Diseases, 70(9):1534-1541, 2011.
Mehlisch, et al., "Comparison of the analgesic efficacy of concurrent ibuprofen and paracetamol with ibuprofen or paracetamol alone in the management of moderate to severe acute postoperative dental pain in adolescents and adults: a randomized, double-blind, placebo-controlled, parallel-group, single-dose, two-center, modified factorial study," Clinical Therapeutics, 35(5):882-895, 2010.
Merry, et al., "Combined acetaminophen and ibuprofen for pain relief after oral surgery in adults: a randomized controlled trial," British Journal of Anaesthesia, 104(1):80-88, 2010.
Merry, et al., "Randomized comparison between the combination of acetaminophen and ibuprofen and each constituent alone for analgesia following tonsillectomy in children," Canadian Journal of Anaesthesia, 60(12):1180-1189, 2013.
Mehlisch, D. et al., "Comparison of the Analgesic Efficacy of Concurrent Ibuprofen and Paracetamol with Ibuprofen or Paracetamol Alone in the Management of Moderate to Severe Acute Postoperative Dental Pain in Adolescents and Adults: A Randomized, Double-Blind, Placebo-Controlled, Parallel-Group, Single-Dose, Two-Center, Modified Factoria Study," Clinical Therapeutics, vol. 32, No. 5, pp. 882-895, 2010.
Merry, A., et al., "Combined Acetaminophen and Ibuprofen for Pain Relief after Oral Surgery in Adults: a Randomized Controlled Trial," British Journal of Anaesthesia, vol. 104, No. 1, pp. 80-88, 2010.
Moore, R., et al., "Validating Speed of Onset as a Key Component of Good Analgesic Response in Acute Pain," European Journal of Pain, No. 19, pp. 187-192, 2015.
U.S. Appl. No. 13/062,985, Office Action, dated Jan. 19, 2012.
U.S. Appl. No. 13/062,985, Office Action, dated Nov. 19, 2013.
U.S. Appl. No. 13/062,985, Office Action, dated May 14, 2015.
U.S. Appl. No. 13/062,985, Office Action, dated Dec. 4, 2015.

\* cited by examiner

COMBINATION COMPOSITION

CROSS-REFERENCE TO RELATED APPLICATIONS

This application is a continuation of U.S. patent application Ser. No. 11/570,887, filed Dec. 19, 2006, now pending, which is a 35 U.S.C. § 371 National Stage of International Application No. PCT/NZ2005/000168, filed Jul. 7, 2005, which claims priority to New Zealand Patent Application No. 533982, filed Jul. 7, 2004. The foregoing applications are incorporated herein by reference in their entireties.

TECHNICAL FIELD

The invention relates to a method and combination composition for the treatment of pain, in particular, the invention relates to a composition containing ibuprofen and paracetamol for the treatment of pain.

BACKGROUND TO THE INVENTION

Without a medical practitioner's prescription (ie over the counter ("OTC")), a full therapeutic dose of paracetamol (acetaminophen) is 1000 mg, a full therapeutic dose of ibuprofen is 400 mg to relieve pain. The total daily amount is also limited to 4000 mg of paracetamol and 1200 mg of ibuprofen, per day in divided doses.

Dosing regimes for each of paracetamol and ibuprofen, when given individually to patients, are often maximised to give the full individual therapeutic dose. Care needs to be taken that the maximum daily dose is met but not exceeded for each medication.

Pharmaceutical combinations such as paracetamol and codeine (500 mg/8 mg) and ibuprofen and codeine (200 mg/12.8 mg) in single dose forms are known. Avoiding use of codeine can be an advantage due to constipation difficulties that are a common side effect.

Combinations of paracetamol, ibuprofen and codeine are known in South Africa, with a single tablet including paracetamol 250 mg, ibuprofen 200 mg, codeine 10 mg. Another combination of paracetamol, aspirin and codeine is also known in a single doss form including 325 mg paracetamol, 325 mg aspirin and 10 mg codeine. In both cases, at a dose of two capsules, sub-therapeutic doses of paracetamol are delivered. In the case of the South African combination, while 4 capsules would give a full OTC therapeutic dose of paracetamol, the amount of ibuprofen would then exceed allowed OTC dose limits.

Paracetamol can be taken without prescription in dosages of 500-1000 mg every 4 to 6 hours up to 4 g/day for the treatment of fever/pain. Ibuprofen is taken without prescription in doses of 200-400 mg every 6 hours up to 1200 mg/day for analgesia.

Ibuprofen is generally well tolerated in divided self medicated doses of up to 1.2 g/day, but it is still associated with side effects in some individuals, such as gastro-intestinal damage. (Reference: Schelman J M et al 2004—A randomised controlled comparison of ibuprofen at maximal over-the-counter dose compared with prescription-dose celecoxib on upper gastrointestinal mucosal injury. Clin Gastroenterol Hepatol 2(4): 290-5) and a a number of other adverse effects (reference: AHFS Drug Information, 2004).

Paracetamol, however, is regarded as "relatively non-toxic in therapeutic doses" (AHFS Drug Information 2004).

The literature has reported that for some drugs the frequency of dosing is more important in determining adverse reactions rather than total dose (I R Edwards, Pharmacological Basis of Adverse Drug Reactions, Chapter 6, page 293 in Avery's Drug Treatment, 1996, $4^{th}$ edn: Adis International, Auckland). This suggests that giving 2×150 mg ibuprofen four times a day rather than 2×200 mg three times a day may be better tolerated. This type of principle is also in part behind that of sustained release products where drug is gradually released avoiding such extreme peak and trough effects from immediate release dose forms. It is also conceivable that decreasing the amount of ibuprofen given as a single dose will improve the tolerability of ibuprofen.

However, it is a concern that using a lower dose of ibuprofen would result in less pain relief due to a lower peak drug concentrations with the result that the efficacy of the pain relief is reduced.

There would be an advantage to be able to deliver these medications in combination at a high therapeutic dose in order to minimise the number of doses required throughout the day, while still achieving the maximum daily dose rate per day for more effective pain relief. Reduction of the amount of ibuprofen to reduce the likelihood of side effects occurring while maintaining pain relief effect and minimising doses needed would achieve those advantages. The ability to achieve effective pain relief from such a combination to treat short term, intermittent, type pain would also be an advantage. Such a combination has not been previously provided and the concept would allow a number of advantages to be achieved, such as convenience of administration, increased ease of user compliance, and effective pain relief over time.

SUMMARY OF THE INVENTION

In broad terms the invention in a first aspect may be seen to comprise a combination composition for the treatment of pain including about 125 mg to about 150 mg ibuprofen and about 475 mg to about 500 mg paracetamol.

Preferably the ratio of paracetamol:ibuprofen is about 50:15.

Preferably the composition includes 150 mg ibuprofen and 500 mg paracetamol.

The ibuprofen can be present as a salt, ester or complexed form and the amount is suitable to deliver between about 125 mg to about 150 mg ibuprofen.

Preferably the composition is administered as two unit doses four times a day.

Preferably the unit doses are tablets or capsules.

In another aspect the invention provides a method of pain management including the delivery of between about 250 mg to 300 mg ibuprofen and about 975 mg to about 1000 mg paracetamol in a single administration.

In another aspect the invention may be seen to be a method of pain management by providing a dosing regime for the delivery of both paracetamol and ibuprofen wherein the actives are administered in a combination composition, including about 125 mg to about 150 mg ibuprofen and about 476 mg to about 500 mg paracetamol per single dose, and wherein the single dose is given in two unit doses four times daily.

Preferably the unit doses are tablets or capsules.

Preferably the ratio of paracetamol:ibuprofen in the single therapeutic dose is about 50:15.

The ibuprofen can be present as a salt, ester or complexed form and the amount is suitable to deliver between about 125 mg to about 150 mg ibuprofen.

Preferably the composition includes 150 mg ibuprofen and 500 mg paracetamol.

In another aspect the invention provides the use of about 476 mg to about 500 mg paracetamol and about 125 mg to about 150 mg ibuprofen in the manufacture of medicament to be administered in two unit doses four times a day for the treatment of pain.

Preferably the ratio of paracetamol:ibuprofen is about 50:15.

The ibuprofen can be present as a salt, ester or complexed form and the amount is suitable to deliver between about 125 mg to about 150 mg ibuprofen.

Preferably 150 mg ibuprofen and 500 mg paracetamol is used.

In another aspect, the invention provides a pharmaceutical pack including tablets or capsules, each tablet or capsule including a combination composition as described in the first aspect of the invention, the pack including instructions to the user to take two tablets or capsules no more than 4 times a day.

Preferably the pack includes an even number of tablets or capsules.

Preferably the pack includes at least 8 tablets or capsules.

In another aspect the invention provides a pharmaceutical composition for the treatment of pain, the composition including paracetamol and ibuprofen in a synergistically effective ratio of paracetamol:ibuprofen of between about 42.5:12.5 to about 50:15.

Preferably the ratio is 50:15.

The composition can be present as a salt, ester or complexed form of ibuprofen in an amount sufficient to deliver ibuprofen to the user in the stated ratio range.

Preferably the composition is a tablet or capsule.

Preferably the composition is administered four times a day.

DETAILED DESCRIPTION OF THE INVENTION

The invention in broad terms relates to a pharmaceutical preparation including both ibuprofen and paracetamol which is suitable for oral administration for the treatment of pain, and which can be taken without undue difficulty. In particular the pharmaceutical preparation is for the temporary relief of pain such as headache, period pain and musculoskeletal pain. When afflicted by such pain it would be an advantage to be able to administer a full daily OTC ("over the counter") therapeutic dose of both of the pain relief actives in a dose regime that allows the maximum daily doses to be met but not exceeded.

The pharmaceutical preparation according to the invention combines paracetamol and ibuprofen. Delivery of maximum therapeutic doses in a combination composition of paracetamol and ibuprofen would require 1000 mg of paracetamol and 400 mg of ibuprofen. If delivered in this combination four times daily to give the maximum daily dose of 4000 mg of paracetamol, the corresponding amount of ibuprofen delivered per day would be 1600 mg, 400 mg in excess of the maximum rate of 1200 mg. A reduction to three doses a day of the maximum therapeutic dose would give the maximum daily dose of ibuprofen, but would result in inefficient use of the paracetamol which at a daily amount of 3000 mg would fall short of the maximum daily amount allowed of 4000 mg.

The combination composition according to the invention includes about 125 mg to about 150 mg ibuprofen and about 475 mg to about 500 mg paracetamol. This allows the composition to be taken 4 times a day resulting in full OTC levels per day to be administered but with lower peak levels of ibuprofen. This offers the prospect of reduced incidence of adverse side effects than can result from ibuprofen use but carries the risk that the pain relief may be lower and, as a result, inadequate. It has been surprisingly found that when the ibuprofen/paracetamol combination is administered in the amount and with the regime according to the present invention there appears to be little or no reduction in the pain relief effect. In fact the pain relief is very much improved over the same amount of ibuprofen administered alone. It is therefore possible to mitigate the potential for adverse side effects due to high peak ibuprofen use while maintaining or improving the pain reduction effect. It is hypothesised that the observed efficacy of the combination may be due to a synergistic reaction occurring between the paracetamol and the ibuprofen, following administration.

The inventors have therefore recognized that an adjustment of the ratio of paracetamol to ibuprofen would maximise the efficiency with which a combination composition could be given to ensure that the individual therapeutic doses are of a concentration strong enough to deliver effective pain relief, while resulting in the maximum daily allowance. By reducing the amount of ibuprofen in the composition to an amount less than the recommended maximum single therapeutic dose, it can be given more frequently throughout the day to result in the maximum daily amount being given. This allows a combination composition containing about 1000 mg of paracetamol and about 300 mg of ibuprofen (about 500 mg paracetamol+about 150 mg ibuprofen in 2 pills/capsules) to be given four times daily, resulting in the maximum daily amount given for each medication. The expected detriment is that the amount of ibuprofen administered per dose is lower thus it would be expected that pain relief will not be sufficient or at least lower. As stated earlier, it has been surprisingly found that this is not the case. Pain relief is consistently of at least equivalent efficacy.

It has also been surprisingly found that the composition (paracetamol:ibuprofen ratio between about 47.5:12.5 and about 50:15; preferably 50:15) provides enhanced pain relief during the first dose interval in comparison to the individual actives when taken alone. This effect of itself provides options for pain management in situations where continued administration may be unnecessary. The user obtains effective pain relief being able to ingest reduced levels of ibuprofen. To achieve this effect it is very much preferred that the lowest individual adult dose of ibuprofen will be about 250 mg taken with about 950 mg paracetamol (eg in 2 tablets/pills with 125 mg ibuprofen and 475 mg paracetamol in each pill). The largest amount of actives will be dependent on practical aspects such as safety aspects relating to the maximum OTC amount per day and the size of the resultant pill/capsule. Preferably the amount of actives in a single pill/capsule will be about 150 mg ibuprofen and 500 mg paracetamol. Two such pills/capsules would be taken to provide a single dose of 300 mg ibuprofen and 100 mg paracetamol. While pills/capsules containing more than 500 mg paracetamol and 150 mg ibuprofen could be made, such options are not preferred due to the size of the pill/capsule and resultant ingestion and compliance difficulties.

As would be known to the skilled person, pharmaceutical acceptable salts or esters of the two actives could also be used. For example, ibuprofen is usually given as the acid but various salts, esters and other complexes are also used. These include lysine and sodium salts, guaiacol and pyridoxine esters, and aminoethanol, isobutanolammonium, and meglumine derivatives. Ibuprofen is usually administered as a racemic mixture but preparations containing only the S(+)-isomer (dexibuprofen) are available in some countries.

As will be apparent, when a salt form is used in the formulation sufficient will need to be included to meet the desired amount of acid (eg 342 mg ibuprofen lysinate=200 mg ibuprofen).

In a preferred form the active ingredients (paracetamol: ibuprofen) are formulated in the ratio of about 50:15 in a single tablet or capsule in amounts by weight which are suitable to be administered four times a day to meet the recommended maximum dose (without medical practitioner's prescription) without excessive tablet or capsule administration. Given the weight amounts of the components that can be used, it is preferable that the pharmaceutical preparation is given in two tablets or capsules for ease of ingestion by the user. If has been found that it is possible to formulate a preparation that includes paracetamol (500 mg) and ibuprofen (150 mg) in a single tablet or capsule. Thus two tablets/capsules four times a day (ie in a 24 hour period; preferably qid) will deliver the maximum allowed daily dose.

While effective pain management can be achieved within the first dose interval, it is preferred to couple this with a quarterly administration regime. This new combination of component amounts and dosing regime allows for a simple, effective, and achievable self-medication for pain relief thus overcoming problems that can occur with self medication requirements. Such problems will include ease of compliance with the required dosing regime. Two tablet or capsules four times a day is a relatively easy regime to be met by a user. Increasing from this amount can result in dosage and administration problems. This is an additional advantage to that of the potential for reduction in occurrence of adverse side effects. The amount of ibuprofen and paracetamol could be adjusted to slightly lower levels if desired, in order to maintain a safety margin from a daily dose perspective. The amount of ibuprofen (as the acid) in a single dose would therefore be between about 125 mg and about 150 mg; and the amount of paracetamol between about 475 mg and about 500 mg. Acceptable pharmaceutical variations are intended to be covered.

The ingredients will be formulated into a tablet or capsule using known pharmaceutical carriers and excipients. Preferably they will be formulated into a film-coated tablet of a size capable of containing the amounts of ingredient preferred. Preferably this will be oval for ease of swallowing and film coated. The composition can also be administered in, for example, two 00 size capsules. In a less preferred aspect, the actives could be administered as separate unit doses. The result would for example be the administration of two 500 mg paracetamol pills/capsules and two 150 mg ibuprofen pills/capsules. This is less preferred as the administration of four pills/capsules is not conducive to compliance.

Essentially, by using a ratio of about 50:15 (eg 500 mg paracetamol:150 mg ibuprofen) a full OTC daily therapeutic dose (non-prescription) can be conveniently provided to the user in two tablets/capsules for ingestion 4 times a day (ie 6 hourly). The ingestion of higher numbers of pills in a single dose is impractical and tends to meet consumer resistance.

In a preferred form, the tablet containing the active ingredients would be created using pharmaceutically acceptable ingredients including maize starch, colloidal silicon dioxide, disodium EDTA, polyvinyl pyrrolidine, sodium benzoate, colloidal silicon dioxide, magnesium stearate, sodium starch glycollate. Other pharmaceutically acceptable ingredients as would be known to the skilled person could also be used.

The paracetamol may be provided in either powder or crystalline form.

The ibuprofen may be provided in any suitable particle size such as either 25 micron or 50 micron particle size.

Purified water will preferably be used when preparing the formulation.

The tablets/capsules ("pills") will preferably be presented to the consumer as part of a pharmaceutical pack, such as a blister pack, as will be well known. The pack should have an even number of pills, preferably at least 8 pills, contained within it and have instructions to take 2 pills no more than 4 times per day (ie in a 24 hour period). Preferably the instructions will be to take the pills at 6 hourly intervals (ie qid). It is of course possible that the pills could be sold contained in a bottle, the pills held loosely within that bottle.

EXAMPLES

Example 1: Tablets for Oral Use

| Core | |
|---|---|
| Paracetamol | 500.0 mg |
| Ibuprofen | 150.0 mg |
| Maize Starch (dry mix) | 14.83 mg |
| Colloidal Silicon Dioxide | 1.70 mg |
| Maize Starch (for paste) | 22.5 mg |
| Disodium EDTA | 0.50 mg |
| Polyvinyl Pyrrolidone | 7.54 mg |
| Sodium Benzoate | 1.00 mg |
| Maize Starch (Lubrication) | 12.50 mg |
| Colloidal Silicon Dioxide | 12.00 mg |
| Magnesium Stearate | 2.45 mg |
| Sodium Starch Glycollate | 25.00 mg |
| Purified Water | q.s. |
| Coating | |
| Hydroxypropylmethyl cellulose | 7.20 mg |
| Polyethylene Glycol 6000 | 0.80 mg |
| Titanium Dioxide (Colourant) | 0.21 mg |
| Methylhydroxybenzoate | 0.20 mg |
| Propylhydroxybenzoate | 0.02 mg |
| Purified Water | q.s. |
| Total | 758.45 mg |

Example 2: Preparation of Tables

A. Preparation of a Granulation Mixture
1. Weigh paracetamol and ibuprofen and sift using a suitable vibrosifter and transfer to mixer. Discard any material not passing through #12 sieve.
2. Weigh and sift maize starch using a suitable vibrosifter (#40 sieve) and transfer to mixer.
3. Weigh and sift colloidal silicon dioxide using a suitable vibrosifter (#100 sieve) and transfer to mixer.
4. Mix for 10-11 minutes at slow speed.

B. Wet Granulation and Drying
1. Add purified water (0.03 ml/tablet) to stainless steel container
2. Sift maize starch (for paste) using suitable sieve (for example #60) and stir until slurry is formed.
3. Add purified water (0.18 ml/tablet) to a suitable jacketed planetary mixer and heat to boiling.

4. Add disodium EDTA, polyvinyl pyrrolidine and sodium benzoate. Dissolve and stir for 5-6 minutes until a clear solution is obtained.
5. Add starch slurry under continuous stirring until a translucent paste is obtained.
6. Cool paste to 50-55° C. by circulating cool water in the jacket of the planetary mixer.
7. Slowly add the paste to a high speed granulator, mix at slow speed, then high speed until consistency is achieved.
8. Unload wet granules into the Fluid Bed Dryer, keeping mixer and chopper at slow speed followed by fast speed. Dry until Loss on Drying value is not more than 1% w/w C. Dry Sifting, Milling and Lubrication
1. Screen dried granules through a suitable multimill and with a 2.5 mm screen. Re-mill remaining granules.
2. Check theoretical yield (99-100%)
3. Weigh and sift through 40 mesh sieve on a suitable vibro-sifter, sodium starch glycollate, magnesium stearate, colloidal silicon dioxide and maize starch (for lubrication) through a 100 mesh sieve. Transfer lubricants to dried granules and mix for 5 minutes at 25 rpm in a suitable mixer.
4. Check theoretical yield (99-100%).

E. Tablet Compression, Film Coating and Polishing
1. Compress on a rotary press using specified punches into tablets
2. Add coating ingredients, Hydroxypropylmethyl cellulose, Polyethylene Glycol 6000, Titanium Dioxide (Colourant), Methylhydroxybenzoate, Propylhydroxybenzoate to water to form a slurry (10-12% w/v).
3. Coat tablets in a suitable auto-coater. Set spray guns (3) at a suitable rate e.g. 35 mls/minute i.e. 105 mls/min and coat tablets.
4. Polish final tablets with wax (beeswax 0.1 mg/tablet and carnuba wax 0.3 mg/tablet. Sprinkle mixed waxes over tablets and rotate for about 10 minutes.

The tablets satisfy the disintegration time requirements of the Ph.Eur. and USP.

Example 3: Tablets for Oral Use

| Part 1 (Dry Mixing) | |
|---|---|
| Paracetamol | 500.0 mg |
| Ibuprofen | 150.0 mg |
| Maize Starch (dry mix) | 25.32 mg |
| Microcrystalline Cellulose | 30.00 mg |
| Pregelatanised starch | 32.00 mg |
| Croscarmellose sodium | 2.50 mg |
| Part II (Granulation) | |
| Maize starch (paste) | 50.00 mg |
| Methyl parahydroxybenzoate | 0.30 mg |
| Propyl parahydroxybenzoate | 0.03 mg |
| Purified Water | q.s. |
| Part III (Lubrication) | |
| Maize starch | 10.00 mg |
| Croscarmellose sodium | 10.00 mg |
| Magnesium stearate | 4.85 mg |
| Talc | 10.00 mg |
| Film Coating | |
| Opadry white OYLS 58900 | 14.00 mg |
| Talc | 1.00 mg |
| Purified Water | q.s. |

Example 4: Preparation of Tablets of Example 3

Part I
1. Transfer, sieve & blend into a suitable stainless steel high speed mixer granulator—Paracetamol, ibuprofen, maize starch, microcrystalline cellulose, pregelatanised starch and croscarmellose sodium. Mix for 10 minutes.

Part II
1. Transfer into a stainless steel container purified wafer (amount equivalent to 6.00 L/120,000 tablet batch) and maize starch, stir to obtain a uniform slurry.
2. Transfer wafer (30.00 L/120,000 tablet batch) into a stainless steel paste kettle, heat to boiling and dissolve Methyl parahydroxybenzoate and Propyl parahydroxybenzoate.
3. Add starch slurry under constant stirring for gelatinisation.
4. Slowly add starch paste to mixture from Part I in a high speed mixer granulator. Run the mixer blade slowly for 10-20 minutes, then simultaneously run the agitator at slow speed and chopper at fast speed for 5-7 minutes.
5. Granulate the above weight mass by using a multimill equipped with 8 mm screen, knives forward, medium speed.
6. Dry the wet granulate in a fluid bed dryer at 52-55° C. until the LOD value is obtained in between 2.5-3.3% w/w.
7. Sieve the dried granulate through a sifter equipped with a 20 mesh sieve and oversize through multimill with 1.5 mm screen, knife forward, medium speed arrangement.

Part III: Final Fixture
1. Transfer the milled granules to inprocess bin blender
2. Sift the maize starch, croscarmellose sodium and purified talc & transfer to the milled granules.
3. Mix for 4 minutes at slow speed, keeping chopper in off position & record premix time.

Tabletting
1. Compress the final mixture by a tabletting machine, equipped with a capsule shaped punches, to obtain a weight of 825 mg per tablet.

Preparation of Film Coating

Mix Opadry white, purified talc and wafer (13.20 L/120,000 tablet batch), stir for 10 minutes, check weight, add more water if necessary to get required weight, filter suspension through 100# nylon cloth.

Film Coating
1. Coat the compressed tablets in a coating pan with coating suspension.
2. Polish the coated tablets in a coating pan with purified talc The tablets satisfy the disintegration time requirements of the Ph.Eur. and USP.

Example 5

The combination of Example 3 was tested in a pilot study using a dental pain model i.e. patients were given either 2 Paracetamol 500 mg+Ibuprofen 150 mg tablets four times a day or 2 150 mg tablets containing ibuprofen alone four times a day for analgesia following wisdom tooth extraction under local anaesthesia. Pain scores at rest and on activity were measured by visual analogue scales which were used to derive an area-under-the curve (AUC) pain score. A lower AUC represents better pain relief.

The results shown in Table 1 are surprising in that despite limited patient numbers the combination of Paracetamol 500 mg+ibuprofen 150 mg demonstrated a very clear superiority in pain relief over ibuprofen alone in all parameters.

TABLE 1

| Treatment | AUC Pain Score (mm × mins) | |
| --- | --- | --- |
| | Rest | Activity |
| Ibuprofen (N = 2) | | |
| Mean | 34,105 | 40,015 |
| Median | 34,105 | 40,015 |
| Minimum | 11,335 | 12,368 |
| Maximum | 56,876 | 67,662 |
| Maxigesic (N = 3) | | |
| Mean | 9,970 | 10,053 |
| Median | 3,780 | 3,510 |
| Minimum | 0 | 0 |
| Maximum | 26,130 | 26,650 |

The present invention allows effective pain relief to be achieved using reduced ibuprofen amounts in combination with paracetamol. Minimisation of potential adverse reactions from high peak amounts of ibuprofen is achieved as a result. The composition allows a pain management regime to be set up that is achievable and effective for an individual, and which can be provided without prescription.

Example 6

Table 2 below provides a comparison of mean visual analogue pain scores (VAS scores) for ibuprofen only, paracetamol only and ibuprofen+paracetamol compositions in a dental pain model. A lower VAS score is consistent with less pain due to better pain relief. The VAS scores for the ibuprofen only, and the ibuprofen+paracetamol (Maxigesic), compositions have been calculated from the AUC trials as reported in Example 5. Pain scores were calculated as means over the first dose interval rather than AUC values to allow comparison with literature values for paracetamol in the dental pain model.

TABLE 2

| Treatment Group | Mean Pain Score at Rest (over first dose interval) |
| --- | --- |
| Ibuprofen 300 mg qid | 28 mm |
| Maxigesic qid (Paracetamol 1000 mg + Ibuprofen 300 mg) | 8 mm |
| Paracetamol 1000 mg (RA Seymour et al 2003) | 42 mm (over 4 hours) |
| | 46-48 mm (0-30 minutes) |

Paracetamol reference: R A Seymour et al. An investigation into the comparative efficacy of soluble aspirin and solid paracetamol in postoperative pain after third molar surgery. Br Dental J (2003) 194(3), 153-7. Compares pain after dental surgery for 240 minutes after dosing. Patients took paracetamol 1000 mg or aspirin soluble 900 mg.

The effectiveness of the ibuprofen+paracetamol combination (Maxigesic) in comparison to the actives alone, as reflected in VAS score comparison, is clearly seen. This enhanced pain relief effect over the first dose interval is unexpected and offers advantages in pain relief management to the user. The observed increase in effective pain relief of the combination over the first pain interval, at reduced ibuprofen amounts, offers pain management options for users when treating intermittent pain with a single dose administration. The enhanced effect reinforces the results observed for the daily administration (4 times a day for maximum OTC administration) and shows that, at the ratios of actives used in the treatment (is between about 47.5:12.5 to about 50:15; preferably about 50:15; paracetamol:ibuprofen), a synergistic pain relief effect is occurring.

While in the foregoing description there has been made reference to specific components or integers of the invention having known equivalents then such equivalents are herein incorporated as if individually set forth.

Although this invention has been described by way of example only and with reference to possible embodiments thereof it is to be understood that modifications or improvements may be made without departing from the scope or spirit of the invention as defined in the attached claims.

The invention claimed is:

1. A method for treating acute pain comprising administering 250 mg to 300 mg ibuprofen and 975 mg to 1000 mg paracetamol in a single administration, wherein the ratio of paracetamol to ibuprofen administered is 50:15 and the administration comprises administering tablets or capsules, wherein each tablet or capsule comprises both ibuprofen and paracetamol and the ratio of paracetamol to ibuprofen in each tablet or capsule is 50:15.

2. The method of claim 1, comprising administering 300 mg ibuprofen and 1000 mg paracetamol in the single administration.

3. The method of claim 1, comprising administering 292.5 mg ibuprofen and 975 mg paracetamol in the single administration.

4. The method of any of claims 1-3, wherein the administration occurs four times daily.

* * * * *